United States Patent [19]

Zimmerman et al.

[11] Patent Number: 4,826,930
[45] Date of Patent: May 2, 1989

[54] MELAMINE-DIAMINE CONDENSATES AND THE CURE OF 1,2-EPOXIDE RESINS THEREWITH

[75] Inventors: Robert L. Zimmerman; Harold G. Waddill; George P. Speranza, all of Austin, Tex.

[73] Assignee: Texaco Chemical Company, White Plains, N.Y.

[21] Appl. No.: 184,733

[22] Filed: Apr. 22, 1988

[51] Int. Cl.[4] .............................................. C08G 59/50
[52] U.S. Cl. ...................................... 525/504; 528/111; 528/361; 528/373; 528/118; 528/407; 544/196
[58] Field of Search ................ 544/196; 528/111, 407, 528/361, 373; 525/504

[56] References Cited

U.S. PATENT DOCUMENTS

| | | | |
|---|---|---|---|
| 2,414,289 | 1/1947 | Ericks | 544/196 X |
| 3,380,881 | 4/1968 | Williamson et al. | 528/111 X |
| 3,679,589 | 7/1972 | Schnegelberger et al. | 544/196 X |
| 4,116,938 | 9/1978 | Schulze et al. | 528/111 X |
| 4,127,514 | 11/1978 | Waddill | 528/111 X |
| 4,179,552 | 12/1979 | Waddill | 528/111 |
| 4,356,304 | 10/1982 | Szita et al. | 544/196 |
| 4,436,891 | 3/1984 | Umeda et al. | 528/111 |

Primary Examiner—Earl Nielsen
Attorney, Agent, or Firm—Jack H. Park; Kenneth R. Priem; Carl G. Ries

[57] ABSTRACT

Novel melamine-poly(oxyethylene or oxypropylene) diamine condensates are prepared which have the formula:

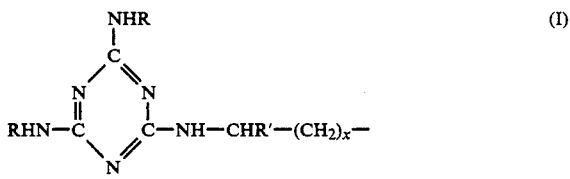

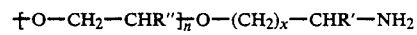

Wherein:
R represents H or

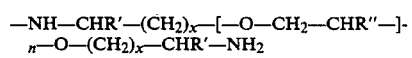

R' represents H or —CH$_3$,
R" represents H or —CH$_3$ or CH$_2$CH$_3$,
x represents an integer having a value of 1 or 2, and
n is a number having an average value of about 1 to about 2.

The melamine-poly(oxyethylene or oxypropylene) diamine condensates have utility as curing agents for epoxy resins.

18 Claims, No Drawings

MELAMINE-DIAMINE CONDENSATES AND THE CURE OF 1,2-EPOXIDE RESINS THEREWITH

BACKGROUND OF THE INVENTION

Technical Field of the Invention

This invention relates to condensates of melamine and polyoxyethylene diamines or polyoxypropylene diamines. More particularly, this invention relates to novel condensates prepared by reacting from about 1 to about 6 mole equivalents of a polyoxyethylene diamine or a polyoxypropylene diamine with 1 mole of melamine under acid conditions to thereby provide a melamine condensate containing about 1 to 3 polyoxyethylene or polyoxypropylene amino groups per melamine group. The reaction is conducted under acid conditions and preferably using an acidic catalyst such as a catalyst prepared by depositing phosphoric or phosphorous acid on a carrier such as titania, zirconia, silica, etc. The reaction is preferably conducted at autogeneous pressure at a temperature within the range of about 150° to about 250° C.

The melamine condensates of the present invention have unique utility as curing agents for 1,2-epoxide resins in that the condensates cure at two separate temperature levels making it possible to prepare a stable "B" stage (partially cured) 1,2-epoxy resin composition which can be stored until needed and then cured with the application of heat and, pressure, if necessary.

Prior Art

Lee and Neville, in their text, *Handbook of Epoxy Resins*, on pages 10–14 thereof disclose the use of melamine and N,N'-diallylmelamine as epoxy curatives.

It is also known that polyoxyalkylene diamines of the type used as starting materials for the preparation of the condensates of the present invention can be used as curing agent for epoxy resins as shown, for example, by Yeakey U.S. Pat. No. 3,654,370. This is further elaborated on, for example, in a Technical Bulletin published by Texaco Chemical Company in 1978 entitled "JEFFAMINE ®" polyoxypropyleneamines. See also Sellstrom et al. U.S. Pat. Nos. 4,514,530, 4,552,933, 4,574,143 and 4,578,412.

Waddill et al. in their U.S. Pat. No. 4,665,191 have also proposed the preparation of Mannich condensates useful as 1,2-epoxide curing agents which are prepared by reacting an imidazole and formaldehyde with a polyoxyalkylenepolyamine.

SUMMARY OF THE INVENTION

It has been surprisingly discovered in accordance with the present invention that a new class of melamine condensates can be prepared when melamine is reacted under acid conditions at a temperature within the range of about 150° to about 250° C. with about 1 to 6 mole equivalents of a polyoxyethylene diamine or a polyoxypropylene diamine having the formula:

$$H_2N-CHR'-(CH_2)_x-[-O-CH_2-CHR''-]_n-O-(CH_2)_x-CHR'-NH_2 \quad (II)$$

Wherein:
R' represents H or —CH$_3$,
R" represents H or —CH$_3$ or —CH$_2$CH$_3$,
x represents an integer having a value of 1 or 2, and
n is a number having an average value of about 1 to about 2.

The thus-prepared condensates are novel compositions of matter having the formula:

$$\text{(I)}$$

(structure showing triazine ring with NHR, RHN—C, C—NH—CHR'—(CH$_2$)$_x$—[—O—CH$_2$—CHR"—]$_n$—O—(CH$_2$)$_x$—CHR'—NH$_2$)

Wherein:
R represents H or

—NH—CHR'—(CH$_2$)$_x$—[—O—CH$_2$—CHR"—]$_n$—O—(CH$_2$)$_x$—CHR'—NH$_2$

R' represents H or —CH$_3$,
R" represents H or —CH$_3$ or —CH$_2$CH$_3$,
x represents an integer having a value of 1 or 2, and
n is a number having an average value of about 1 to about 2.

THE STARTING MATERIALS

One of the starting materials for the present invention is melamine, a well-known heterocyclic compound having the formula:

(structure of melamine: triazine ring with three NH$_2$ groups)

The poly(oxyethylene or oxypropylene) diamines to be used as starting materials in accordance with the present invention are diamines having the formula:

$$H_2N-CHR'-(CH_2)_x-[-O-CH_2-CHR''-]_n-O-(CH_2)_x-CHR'-NH_2 \quad (II)$$

Wherein:
R' represents H or —CH$_3$,
R" represents H or —CH$_3$ or —CH$_2$CH$_3$,
x represents an integer having a value of 1 or 2, and
n is a number having an average value of about 1 to about 2.

Examples of representative diamines falling within this definition include polyoxyethylenediamines having the formula:

$$H_2N-CH_2-CH_2-O-[-CH_2-CH_2-O-]_n-CH_2-CH_2-NH_2 \quad (IV)$$

Wherein n is an integer having a value of 1 or 2.

The polyoxyethylenediamines are starting materials having formula (I) wherein R' and R" represent H.

Representative examples of polyoxyethylenediamines of formula (IV) include triethylene glycol diamine (n=1), a product sold commercially by Texaco Chemical Company as Jeffamine ® EDR-148, or tetraethylene glycol diamine, a product sold commercially by Texaco Chemical Company under the trade name Jeffamine ® EDR-192.

As another example, the starting material may be a polyoxypropylene diamine wherein, in formula (I) where R' and R" represent —CH$_3$. Compounds of this nature may be characterized as polyoxypropylene diamines having the formula:

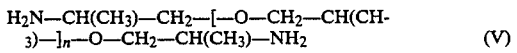

H$_2$N—CH(CH$_3$)—CH$_2$—[—O—CH$_2$—CH(CH$_3$)—]$_n$—O—CH$_2$—CH(CH$_3$)—NH$_2$ (V)

Wherein n is an integer having a value of 1 or 2.

An example of such a product is a polyoxypropylene diamine having an average molecular weight of about 230 (the value of n is between 2 and 3 and which is sold by Texaco Chemical Company under the trade name Jeffamine ® D-230).

In another example, the polyoxyalkylene diamine may be a polyoxy-n-propyl/oxypropylene diamine having formula (VI) given below:

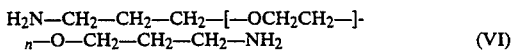

H$_2$N—CH$_2$—CH$_2$—CH$_2$—[—OCH$_2$CH$_2$—]$_n$—O—CH$_2$—CH$_2$—CH$_2$—NH$_2$ (VI)

Wherein n is an integer having a value of 1 or 2.

The reaction between the poly(oxyethylene or oxypropylene) diamines and melamine is conducted under acid conditions which are preferably established by providing a fixed bed of a solid acidic catalyst through which the reactants may be passed in liquid phase. Examples of suitable solid acidic catalysts include pelleted carriers such as titania, zirconia, silica, kieselguhr, silica/alumina, etc., upon which phoshoric acid has been deposited in an amount sufficient to provide from at least 5 to about 45 wt. % of phosphorus.

Preparation of the Melamine-Diamine Condensates

The melamine-poly(oxyethylene or oxypropylene) diamine condensates of the present invention are prepared by reacting melamine with the poly(oxyethylene or oxypropylene) diamines in the proportions of about 2 to 6 mole equivalents of diamine per mole equivalent of melamine.

The reaction is suitably conducted at a temperature of about 150° to about 260° C. under autogeneous pressure. Superatmospheric pressures may be used if desired, but there is no particular advantage in doing so.

The reaction may be conducted batch-wise or in a continuous fashion. When the reaction is conducted on a batch-wise basis, the reaction is preferably conducted in a suitable reaction vessel such as an autoclave to which the melamine and poly(oxyethylene or oxypropylene) diamine reactants are charged together with an appropriate acidic material such as a powdered acid catalyst of the type mentioned above, after which the autoclave is heated to the desired reaction temperature and maintained at that temperature for about 240 to about 6 hours at autogeneous pressure. The reaction product is then filtered and stripped at a temperature of about 150° to about 250° C. and subatmospheric pressure in order to remove unreacted diamine and by-products of the reaction.

If desired, the reaction may be conducted on a continuous basis by passing the melamine and poly(oxyethylene or oxypropylene) diamines over a fixed bed of an acidic catalyst on a continuous basis. In this situation, the reaction should be conducted at the desired temperature of about 150° to about 250° C. and the space velocity should be about 0.2 to about 1.0 g/cc/hr.

Unreacted diamine and by-products of the reaction can be removed from the reaction product by a suitable means such as vacuum distillation.

UTILITY OF THE MELAMINE-POLYOXYALKYLENE DIAMINE CONDENSATES AS EPOXY CURING AGENTS

As indicated, the melamine-polyoxyalkylene diamine condensates of the present invention have unique utility when used as curing agents for 1,2-epoxy resins.

Generally the vicinal epoxide compositions that can be cured using the curing agents of this invention are organic materials having an average of more than one reactive 1,2-epoxide group. These polyepoxide materials can be monomeric or polymeric, saturated or unsaturated, aliphatic, cycloaliphatic, aromatic or heterocyclic, and may be substituted if desired with other substituents besides the epoxy groups, e.g., hydroxyl groups, ether radicals, halogenated phenyl groups and the like.

The most widely used epoxy resins are diglycidyl ethers of bisphenol A:

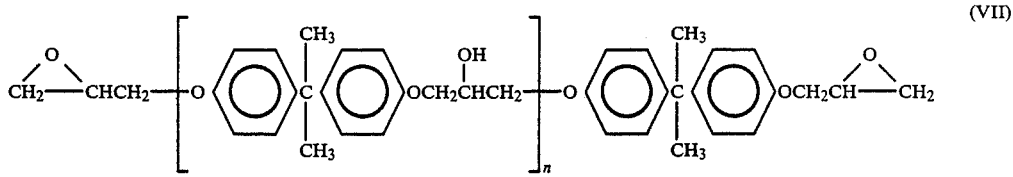

(VII)

where n equals an integer of up to about 10 to 20.

However, these epoxides are representative of the broader class of epoxide compounds that are useful in making epoxy resins.

A widely used class of polyepoxides that can be cured according to the practice of the present invention includes the resinous epoxy polyethers obtained by reacting an epihalohydrin, such as epichlorohydrin, and the like, with either a polyhydric phenol or a polyhydric alcohol. An illustrative, but by no means exhaustive, listing of suitable dihydric phenols includes 4,4'-isopropylidene bisphenol, 2,4'-dihydroxydiphenylethylmethane, 3,3'-dihydroxydiphenyldiethylmethane, 3,4'-dihydroxydiphenylmethylpropylmethane, 2,3'-dihydroxydiphenylethylphenylmethane, 4,4'-dihydroxydiphenylmethane, 4,4'-dihydroxydiphenylbutylphenylmethane, 2,2'-dihydroxydiphenylditolylmethane, 4,4'-dihydroxydiphenyltolylmethyl-methane and the like. Other polyhydric phenols which may also be co-reacted with an epihalohydrin to provide these epoxy polyethers are such compounds as resorcinol, hydroquinone, substituted hydroquinones, e.g., tert-butylhydroquinone, and the like.

Among the polyhydric alcohols that can be co-reacted with an epihalohydrin to provide the resinous epoxy polyethers are such compounds as ethylene glycol, propylene glycol, butylene glycols, pentane diols, bis(4-hydroxycyclohexyl)dimethylmethane, 1,4-dimethylolbenzene, glycerol, 1,2,6-hexanetriol, trimethylolpropane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyhydric thioethers, such as 2,2'-, 3,3'-tetrahydroxydipropylsulfide and the like, mercapto alcohols such as α-monothioglycerol, α,α'-dithioglycerol, and the like, polyhydric alcohol partial esters, such as monostearin, pentaerythritol monoacetate, and the like, and halogenated polyhydric alcohols such as the monochlorohydrins of glycerol, sorbitol, pentaerythritol and the like.

Another class of polymeric polyepoxides that can be cured by means of the above-described curing agents includes the epoxy novolac resins obtained by reacting, preferably, in the presence of a basic catalyst, e.g., sodium or potassium hydroxide, an epihalohydrin, such as epichlorohydrin, with the resinous condensate of an aldehyde, e.g., formaldehyde, and either a monohydric phenol, e.g., phenol itself, or a polyhydric phenol. Further details concerning the nature and preparation of these epoxy novolac resins can be obtained in Lee, H. and Neville, K. "Handbook of Epoxy Resins".

It will be appreciated by those skilled in the art that the polyepoxide compositions that can be cured according to the practice of the present invention are not limited to the above described polyepoxides, but that these polyepoxides are to be considered merely as being representative of the class of polyepoxides as a whole.

The amount of curing agent that is employed in curing polyepoxide compositions will depend on the amine equivalent weight of the curing agent employed. The total number of equivalents of amine group is preferably from about 0.8 to about 1.2 times the number of epoxide equivalents present in the curable epoxy resin composition with a stoichiometric amount being most preferred.

Various conventionally employed additives can be admixed with these polyepoxide-containing compositions prior to final cure. For example, in certain instances it may be desired to add minor amounts of other co-catalysts, or hardeners, along with the curing agent system herein described. Conventional pigments, dyes, fillers, flame retarding agents and other compatible natural and synthetic resins can also be added. Furthermore, known solvents for the polyepoxide materials such as acetone, methyl ethyl ketone, toluene, benzene, xylene, dioxane, methyl isobutyl ketone, dimethylformamide, ethylene glycol monoethyl ether acetate, and the like, can be used if desired, or where necessary.

WORKING EXAMPLES

EXAMPLE 1

To a 5 liter, three-necked flask equipped with a mechanical stirrer, nitrogen atmosphere, thermometer and distillation head was placed 2400 grams (16.2 moles) of triethylene glycol diamine, 340.4 g (2.70 moles) of melamine and 100 g of 30% phosphoric acid on titanium oxide. The reaction was heated to 230° C. and held for 12 hours. It was then filtered to remove catalyst and then stripped at 230° C. and 1 mm Hg vacuum to remove the unreacted EDR-148. The product had the following analysis:

| | |
|---|---|
| Total acetylatables, meq/g | 7.77 |
| Total amine, meq/g | 4.72 |
| Primary amine, meq/g | 4.67 |

EXAMPLE 2

To a 1 liter autoclave was charged 468.9 g (4.5 moles) of bis(aminoethyl)ether, 94.5 g (0.75 moles) of melamine and 20 g of 35% phosphoric acid on silica. The reaction was heated to 240° C. and held for 6 hours. The crude reaction product was then discharged from the autoclave, filtered and stripped to remove the unreacted bis(aminoethyl)ether. There were 247.6 g of product obtained which had the following analysis:

| | |
|---|---|
| Total acetylatables, meq/g | 10.6 |
| Total amine, meq/g | 11.0 |

EXAMPLE 3

To a 2 liter, three-necked flask equipped like Example 1 was placed 131.2 grams (1.04 moles) of melamine, 1000 grams (5.21 moles) of tetraethylene glycol diamine and 25 g of 35% phosphoric acid on silica. The reaction was heated to 235° C. and held for 6 hours. It was then filtered and stripped at 230° C. and 1 mm Hg vacuum. The product had the following analysis:

| | |
|---|---|
| Total acetylatables, meq/g | 5.56 |
| Total amine, meq/g | 5.59 |

EXAMPLE 4

Properties of Epoxy Resin Cured with Melamine-Polyetheramine Condensates

| Formulation | 6213-89A | 6253-6 | 6253-44 |
|---|---|---|---|
| Epoxy resin[1] | 100 | 100 | 100 |
| Melamine-TEG Diamine Condensate (Example 1) | 46 | — | — |
| Melamine-BAEE Condensate (Example 2) | — | 26 | — |
| Melamine-Tetra EG Diamine Condensate (Example 3) | — | — | 54 |
| Properties of Cured ⅛" Casting:[2] | | | |
| Izod impact strength, ft-lbs/in | 0.13 | 0.06 | 0.13 |
| Tensile strength, psi | 11100 | 6100 | 9400 |
| Tensile modulus, psi | 397000 | 407500 | 361000 |
| Elongation at break, % | 12.0 | 1.8 | 9.4 |
| Flexural strength, psi | 17800 | 13800 | 15600 |
| Flexural modulus, psi | 421000 | 415500 | 387000 |
| HDT, °C., 264 psi/66 psi | 84/92 | 108/120 | 70/77 |
| Shore D hardness, 0–10 sec | 82–80 | 84–83 | 82–79 |
| % weight gain, | | | |
| 24 hr water boil | 5.4 | 5.4 | 6.8 |
| 3 hr acetone boil | 1.2 | 0.8 | 2.3 |
| Adhesion Properties:[3] | | | |
| Tensile shear strength, psi | 3800 | 2650 | 4200 |
| T-peel strength, pli | 6.1 | 5.2 | 6.9 |

[1] Liquid epoxy resin of equivalent weight ~185.
[2] Cured overnight ~25° C., 2 hrs. 80° C., 3 hrs. 150° C.
[3] Cured overnight ~25° C., 2 hrs. 150° C.

It will be understood that the foregoing examples are given by way of illustration only and not by way of limitation and that the scope of the present invention is defined solely by the appended claims.

We claim:

1. A composition of matter consisting essentially of a compound having the formula:

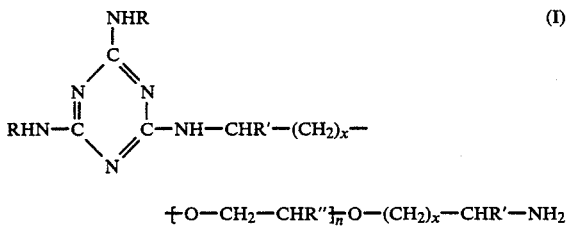

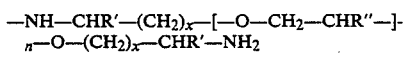

Wherein:
R represents H or

—NH—CHR'—(CH$_2$)$_x$—[—O—CH$_2$—CHR"—]-$_n$—O—(CH$_2$)$_x$—CHR'—NH$_2$

R' represents H or —CH$_3$,
R" represents H or —CH$_3$ or —CH$_2$CH$_3$,
x represents an integer having a value of 1 or 2, and
n is a number having an average value of about 1 to about 2.

2. A composition of matter as in claim 1 wherein R' and R" represent H.

3. A composition of matter as in claim 2 wherein R represents H and n has a value of 1.

4. A composition of matter as in claim 2 wherein R represents H and n has a value of 2.

5. A composition of matter as in claim 1 wherein R' and R" represent —CH$_3$.

6. A composition of matter as in claim 1 wherein R' represents —CH$_2$— and R" represent —CH$_3$.

7. A method for the preparation of a composition which comprises the steps of:
 a. reacting melamine under acid conditions at a temperature of 200° to about 260° C. with an amine having the formula:

H$_2$N—CHR'—(CH$_2$)$_x$—[—O—CH$_2$—CHR"—]-$_n$—O—(CH$_2$)$_x$—CHR'—NH$_2$  (II)

Wherein:
R' represents H or —CH$_3$,
R" represents H or —CH$_3$ or —CH$_2$CH$_3$,
x represents an integer having a value of 1 or 2, and
n is a number having an average value of about 1 to about 2.

8. A method as in claim 7 wherein R' and R" represent H.

9. A method as in claim 8 wherein n has a value of 1.

10. A method as in claim 8 wherein n has a value of 2.

11. A method as in claim 7 wherein R' and R" represent —CH$_3$.

12. A method as in claim 7 wherein x represents 2 and R" represents H.

13. A method for preparing a partially-cured storage-stable 1,2-epoxy resin composition which can subsequently be cured which comprises intimately mixing a 1,2-epoxide resin with an effective amount of an amine curing agent and maintaining said mixture at a temperature of about 20° to about 100° C. whereby amino hydrogens of said amine will react with epoxy groups in said 1,2-epoxide resin by an amount sufficient to provide a cured epoxy resin,
said amine curing agent consisting essentially of a composition having the formula:

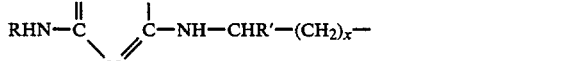

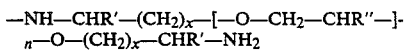

Wherein:
R represents H or

—NH—CHR'—(CH$_2$)$_x$—[—O—CH$_2$—CHR"—]-$_n$—O—(CH$_2$)$_x$—CHR'—NH$_2$

R' represents H or —CH$_3$,
R" represents H or —CH$_3$ or CH$_2$CH$_3$,
x represents an integer having a value of 1 or 2, and
n is a number having an average value of about 1 to about 2.

14. A method as in claim 13 wherein R' and R" represent H.

15. A method as in claim 14 wherein R represents H and n has a value of 1.

16. A method as in claim 14 wherein R represents H and n has a value of 2.

17. A method as in claim 13 wherein R' and R" represent —CH$_3$.

18. A method as in claim 13 wherein R' represents 2 and R" represents H.

* * * * *